(12) United States Patent
Dean (10) Patent No.: US 7,204,805 B2
(45) Date of Patent: *Apr. 17, 2007

(54) PATIENT CONDITIONAL DIAGNOSIS, ASSESSMENT AND SYMPTOM TRACKING SYSTEM

(76) Inventor: Melanie A. Dean, 3800 NW. 72nd St., Kansas City, MO (US) 64151

( * ) Notice: Subject to any disclaimer, the term of this patent is extended or adjusted under 35 U.S.C. 154(b) by 0 days.

This patent is subject to a terminal disclaimer.

(21) Appl. No.: 11/361,504

(22) Filed: Feb. 24, 2006

(65) Prior Publication Data

US 2006/0178569 A1 Aug. 10, 2006

Related U.S. Application Data

(63) Continuation of application No. 10/093,198, filed on Mar. 7, 2002, now Pat. No. 7,008,378.

(51) Int. Cl.
*A61B 5/00* (2006.01)
*G06F 19/00* (2006.01)

(52) U.S. Cl. .......................... 600/300; 705/3
(58) Field of Classification Search ............... 600/300, 600/301; 705/2, 3; 434/262
See application file for complete search history.

(56) References Cited

U.S. PATENT DOCUMENTS

| | | |
|---|---|---|
| 4,837,164 A | 6/1989 | Glick |
| 5,553,609 A | 9/1996 | Chen et al. |
| 5,636,873 A | 6/1997 | Sonsteby |

(Continued)

FOREIGN PATENT DOCUMENTS

WO   WO 01/10298 A2   2/2001

OTHER PUBLICATIONS

Koenig et al., Assessment of Children with Pervasive Development Disorders, Journal of Child and Adolescent Psychiatric Nursing, Oct.-Dec. 2001, vol. 14, Iss.4, p. 159.

(Continued)

*Primary Examiner*—Eric F. Winakur
(74) *Attorney, Agent, or Firm*—Shughart Thomson & Kilroy, PC; Marcia J. Rodgers; Dennis A. Crawford (57) ABSTRACT

A system for diagnosing and tracking patient symptoms includes providing an interview instrument implemented as a computer program accessible by clinician and patient to record symptoms and having diagnostic and assessment information for a selected disorder, the clinician interviewing a patient to identify, assess, and record symptoms on the instrument or the patient recording symptoms on the instrument before the first interview. The clinician develops a diagnosis and treatment plan and records them on the instrument and follows up with interviews for identifying and recording any changes on the instrument for documenting effects of the treatment plan. The interview instrument includes a joint use portion listing symptoms and assessment criteria and space for recording symptoms and assessments, a diagnostic portion having diagnostic criteria for the clinician, a patient-use portion having educational information for the patient and a follow-up portion for tracking effects of a treatment plan across subsequent visits.

13 Claims, 11 Drawing Sheets

U.S. PATENT DOCUMENTS

| | | |
|---|---|---|
| 5,640,549 A | 6/1997 | Powsner et al. |
| 5,772,585 A | 6/1998 | Lavin et al. |
| 5,794,208 A | 8/1998 | Goltra |
| 5,799,981 A | 9/1998 | Tung et al. |
| 5,803,906 A | 9/1998 | Pratt et al. |
| 5,951,300 A | 9/1999 | Brown |
| 6,003,020 A | 12/1999 | Hazlehurst et al. |
| 6,026,363 A | 2/2000 | Shepard |
| 6,122,351 A | 9/2000 | Schlueter et al. |
| 6,139,494 A | 10/2000 | Cairnes |
| 6,434,547 B1 | 8/2002 | Mishelevich et al. |
| 2002/0022975 A1 | 2/2002 | Biasingame et al. |

OTHER PUBLICATIONS

Perrin et al., Clinical Practice Guidline: Treatment of School-Aged Child with Attention-Deficit/Hyperactivity Disorder, Pediatrics, Oct. 2001, vol. 108, No. 4, pp. 1033-1044.

C. Keith Conners, Ph.D., "CADS—Parent Version" 1999, pp. 1-3, Professional Printing & Publishing, Inc. "Distressed Mood/Behavior Intervention Form," 1998, pp. 1-4, USA.

Aaron T. Beck, "BDI-II (Beck Depression Inventory)," 1996, pp. 1-2, USA.

*Fig. 1.*

| 30 © 2001 Compact Clinicals | | | |
|---|---|---|---|
| ADHD Symptom Tracking System - page 1 | | | |
| Patient Name _____ | Parent _____ | | Date _____ |
| ADHD Symptoms of Inattention | If a symptom on the left is a problem, write in an example and check all boxes (for environment) in which the problem occurs. Check how often the problem occurs in the boxes on the right. | | How often does the problem occur? |
| a. often fails to give close attention to details or makes careless mistakes in schoolwork, work, or activities | ❏ home<br>❏ school<br>❏ social<br>❏ self | 32      34 | ❏ Infrequently<br>❏ 1-3 a week<br>❏ 1-3 a day<br>❏ almost all the time |
| b. often has difficulty sustaining attention in tasks or play activities | ❏ home<br>❏ school<br>❏ social<br>❏ self | | ❏ Infrequently<br>❏ 1-3 a week<br>❏ 1-3 a day<br>❏ almost all the time |
| c. often does not seem to listen when spoken to directly | ❏ home<br>❏ school<br>❏ social<br>❏ self | —36— | ❏ Infrequently<br>❏ 1-3 a week<br>❏ 1-3 a day<br>❏ almost all the time |
| d. often does not seem through and fails to finish schoolwork, chores, or duties | ❏ home<br>❏ school<br>❏ social<br>❏ self | | ❏ Infrequently<br>❏ 1-3 a week<br>❏ 1-3 a day<br>❏ almost all the time |
| e. often has difficulty organizing tasks and activities | ❏ home<br>❏ school<br>❏ social<br>❏ self | | ❏ Infrequently<br>❏ 1-3 a week<br>❏ 1-3 a day<br>❏ almost all the time |
| f. often avoids, dislikes or is reluctant to engage in tasks that require sustained mental effort | ❏ home<br>❏ school<br>❏ social<br>❏ self | | ❏ Infrequently<br>❏ 1-3 a week<br>❏ 1-3 a day<br>❏ almost all the time |
| g. often loses things necessary for tasks or activities | ❏ home<br>❏ school<br>❏ social<br>❏ self | | ❏ Infrequently<br>❏ 1-3 a week<br>❏ 1-3 a day<br>❏ almost all the time |
| h. is often easily distracted by extraneous stimuli | ❏ home<br>❏ school<br>❏ social<br>❏ self | | ❏ Infrequently<br>❏ 1-3 a week<br>❏ 1-3 a day<br>❏ almost all the time |
| i. is often forgetful in daily activities | ❏ home<br>❏ school<br>❏ social<br>❏ self | | ❏ Infrequently<br>❏ 1-3 a week<br>❏ 1-3 a day<br>❏ almost all the time |
| Patient Information:<br>Age:<br>Grade:<br>Teacher:<br>Ht:<br>Wt:<br>BP: | Notes<br><br>—50— | | |
| | Assessment Interview | | Complete Both Pages |

Fig. 2.

ADHD Symptom Tracking System - page 2

© 2001 Compact Clinicals

Patient Name ____________________

| ADHD Symptoms of Inattention | If a symptom on the left is a problem, write in an example and check all boxes (for environment) in which the problem occurs. Check how often the problem occurs in the boxes on the right. | | How often does the problem occur? |
|---|---|---|---|
| a. often fidgets with hands or feet or squirms in seat | ☐ home<br>☐ school<br>☐ social<br>☐ self | —32— —34— | ☐ Infrequently<br>☐ 1-3 a week<br>☐ 1-3 a day<br>☐ almost all the time |
| b. often leaves seat in classroom or in other situations in which remaining seated is expected | ☐ home<br>☐ school<br>☐ social<br>☐ self | | ☐ Infrequently<br>☐ 1-3 a week<br>☐ 1-3 a day<br>☐ almost all the time |
| c. often runs about or climbs excessively in situations in which it is inappropriate | ☐ home<br>☐ school<br>☐ social<br>☐ self | —36— | ☐ Infrequently<br>☐ 1-3 a week<br>☐ 1-3 a day<br>☐ almost all the time |
| d. often has difficulty playing or engaging in leisure activities quietly | ☐ home<br>☐ school<br>☐ social<br>☐ self | | ☐ Infrequently<br>☐ 1-3 a week<br>☐ 1-3 a day<br>☐ almost all the time |
| e. often "on the go" or acts as if "driven by a motor" | ☐ home<br>☐ school<br>☐ social<br>☐ self | | ☐ Infrequently<br>☐ 1-3 a week<br>☐ 1-3 a day<br>☐ almost all the time |
| f. often talks excessively | ☐ home<br>☐ school<br>☐ social<br>☐ self | | ☐ Infrequently<br>☐ 1-3 a week<br>☐ 1-3 a day<br>☐ almost all the time |
| g. often blurts out answers before questions have been completed | ☐ home<br>☐ school<br>☐ social<br>☐ self | | ☐ Infrequently<br>☐ 1-3 a week<br>☐ 1-3 a day<br>☐ almost all the time |
| h. often has difficulty awaiting turn | ☐ home<br>☐ school<br>☐ social<br>☐ self | | ☐ Infrequently<br>☐ 1-3 a week<br>☐ 1-3 a day<br>☐ almost all the time |
| i. often interrupts or intrudes on others | ☐ home<br>☐ school<br>☐ social<br>☐ self | | ☐ Infrequently<br>☐ 1-3 a week<br>☐ 1-3 a day<br>☐ almost all the time |

Notes/ Treatment Plan

—52—

Patient agrees with proposed treatment plan _______

Assessment Interview (

Fig. 3.

The ADHD System Tracking System is intended to aid clinicians in assessing and treating ADHD. It is not to be used as the sole basis for diagnoses or treatment of ADHD.

Instructions for Using the ADHD Symptom Tracking System

1. Read the targeted content on this page and the back of pate 2 to learn important diagnostic and assessment information including:
   - DSM-IV diagnostic criteria for ADHD pervasiveness and persistence
   - Assessment techniques for gathering global information required for ADHD diagnosis and treatment planning
   - Strategies for assessing changes due to treatment
2. Ask the patient about specific DSM-IV ADHD symptoms listed in column one of pates 1 & 2.
3. Record the words the patient uses to describe his or her ADHD symptoms. Check the box for each environment in which the symptoms occur. Symptoms of impairment need to occur in two or more environments.
4. Use the symptoms and specific descriptive examples given by the patient to identify target symptoms for treatment.
5. Use the Follow-Up Report to document treatment effects, isolating improved symptoms from those needing continued treatment attention.

DSM-IV Criteria for Attention Deficit Hyperactivity Disorder

A. Six (or more) of either 1) Inattention, or 2) Hyperactivity-impulsivity. Symptoms must have persisted for at least 6 months to a degree that is maladaptive and inconsistent with developmental level:
   1. Inattention:
      a) often fails to give close attention to details or makes careless mistakes in schoolwork, work, or other activities
      b) often has difficulty sustaining attention in tasks or play activities
      c) often does not seem to listen when spoken to directly
      d) often does not follow through on instrucntions and fails to finish schoolwork, chores, or duties in the workplace (not due to oppositional behavior or failure to understand or homework)
      e) often has difficulty organizing tasks and act ivies
      f) often avoids, dislikes, or is reluctant to engage in tasks that require sustained mental effort (such as schoolwork or homework)
      g) often loses thing necessary for tasks or activities (e.g., toys, school, assignments, pencils, books, or tools)
      h) is often easily distracted by extraneous stimuli
      i) is often forgetful in daily activities 2. Hyperactivity-impulsivity:
      Hyperactivity—
      a) often fidgets with hands or feet or squirms in seat
      b) often leaves seat in classroom or in other situations in which remaining seated is expected
      c) often runs about or climbs excessively in situations in which it is inappropriate (in adolescents or adults, may be limited to subjective feelings of restlessness)
      d) often has difficulty playing or engaging in leisure activities quietly
      e) is often "on the go" or often acts as if "driven by a motor"
      f) often talks excessively
      Impulsivity—
      g) often blurts out answers before questions have been completed
      h) often has difficulty awaiting turn
      i) often interrupts or intrudes on others (e.g., butts into conversations or games)
B. Some symptoms causing impairment were present before age 7 years.
C. Some impairment from the symptoms is present in two or more settings (e.g., at school (or work) and at home).

*(DSM-IV Diagnostic Criteria Continued)*
D. There must be clear evidence of clinically significant impairment in social, academic, or occupational functioning.
E. Occurrence is not exclusively during the course of a Pervasive Developmental Disorder, Schizophrenia, or other Psychotic Disorder and are not better accounted for by another mental disorder.

Types:
   Combined Type:
      if both Criteria A1 and A2 are met for the past 6 months
   Predominantly Inattentive:
      if only Criterion A1 is met (not A2) for the past 6 months
   Predominantly Hyperactive-Impulsive Type:
      if only Criterion A2 is met (not A1) for the past 6 months
   Not Otherwise Specified:
      if there are prominent symptoms of inattention or hyperactivity-impulsivity that do not meet full criteria for ADHD

*(Reprinted with permission by the American Psychiatric Association: Diagnostic and Statistical Manual of Mental Disorders, Forth Edition, Washington, DC, American Psychiatric Association, 1994)*

Diagnostic Clarifying Information

Simply knowing that DSM-IV ADHD symptoms are present is not enough for a rigorous and accurate diagnosis. Clinicians should note the following about these symptoms:

- Age of onset of the disorder - Only some symptoms must occur before age seven, but these must be severe enough to create impairment. For example, the clinician may establish that some hyperactive-impulsive symptoms were present in Kindergarten, but if those symptoms created no impairment in social, academic, or home functioning, the age-of-onset criterion would not be met.
- Number and severity of symptoms - DSM-IV requires the presence of at least six of nine hyperactive-impulsive symptoms, and/or six of nine inattentive symptoms. But these symptoms must occur often and they must be "maladaptive and inconsistent with developmental level." The clinician must determine the symptom severity with reference to developmental and normative expectations at a given age.
- Pervasiveness and severity of impairment - Impairment must occur in tow or more settings (e.g., social, academic, or occupational) and there must be evidence that the degree of impairment is "clinically significant." Like symptom severity, clinical significance varies with developmental expectations for age and gender.
- Persistence- The symptoms must have persisted for at least six months with no sustained or intermittent lapses. Symptoms if excitability or inattention could be due to a recent trauma, onset of depression, substance abuse, or organic disease. These clinical significance varies with developmental expectations for symptoms would not count towards ADHD symptom criteria because they did not persist over a six-month period.

ADHD Assessment Techniques

Since there are no definitive ADHD diagnostic tests that clearly demarcate "normal" behaviors from ADHD symptoms, clinicians use a combination of measures to assess ADHD symptoms, impairment, and treatment response including interview and history techniques, observation techniques, standardized assessment measures, and assessing changes due to to treatment.

Interview and History Techniques

Client and parent interviews are the most important methods of assessing The history and symptom picture for ADHD in children and adults. Clinicians need to gather a complete social, medical, and developmental response including interview and history techniques, observation tech-history (from conception to present) to differentiate between situational problems, other diagnoses, and ADHD. This information also impacts treatment planning.

Although it is relatively easy to identify the presence of ADHD symptoms, clinicians find it more difficult to determine whether those symptoms seem excessive fir the client's developmental stage and whether the symptoms are chronic and pervasive enough to warrant and ADHD diagnosis. Thorough interview techniques determine whether the client's behavior differs

*Continued on the back of page 2*

Fig. 4.

Continued from page 1 significantly from "normal" peers. For example, a child who has "difficulty-following through on instructions from others" may do so only in certain situations (school, doing chores), with certain individuals (parents or employers), or when instructions are complex.

To assess impairment, clinicians explore ADHD symptoms in at least four main areas or domains of functioning:
- School or job performance
- Family and home environment
- Social relationships
- Personal functioning (self), including: self-image, belief in one's abilities, and mood — 54

When interviewing, ask for specific examples of each characteristic and its impact on dial functioning. The 18-item DSM-IV symptom list can serve as an interview guide for proving areas of functioning. For example, if the parent agrees that the child, "does not seem to listen...," then the clinician may ask how that affects different life domains such as schoolwork, ability to interact with peers, or playing sports. Specific examples articulated in the client's own words help determine the effects of ADHD on client functioning and are also the basis for evaluating change due to treatment interventions. Additionally, to aid in diagnosis, clinicians often ask parents and teachers to complete standardized rating scales such as the Conners Parent and Teacher Rating Scales.

School or Job Performance — 56

Assessing School Performance in Children- Because children frequently minimize the severity or significance of their difficulties, parent and teacher input is essential to diagnosis. Listed below are a number of validated tools and techniques for assessing school-related aspects of
- Teacher rating scales are usually the most efficient way to provide critical information. During an initial assessment, such scales should cover at least one month of the child's functioning with a particular classroom teacher. In follow-up assessments, shorter periods with more targeted scales may be used in assessing changes due to treatment interventions.
- Grades and report cards provide significant ADHD-related indicators. Look for comments about impulsiveness, disruptive behavior, or attendance. These indicators help determine if poor grades stem from ADHD or actual skill deficits.
- Homework assignments frequently allow parents to clearly observe a child's work habits and skills deficits. Changes in grades stem from ADHD or actual skill deficits.
- The amount of frustration, stress, and struggle related to school or homework often indicates a child's inability to stay on task, work independently, and self-correct mistakes. However, the clinician must determine whether these signs reflect an attention deficit, a learning disability, or teaching materials poorly suited to the child's ability.
- A poor fit between the child's capabilities and the level of instruction is the most common reason for poor school work. — 62 Someone who is a poor reader could have a learning disability in reading and display poor attention because of frustrations, or could be a poor reader because of concentration difficulties due to ADHD.
- Poor peer relationships at school often reflect poor social skills due to problems obeying rules (impulsivity) during play activities.

Assessing Job Performance in Adults- Adults can be poor reporters of their behavior at home and at work. Therefore, whenever possible, include a significant other (e.g., spouse, roommate, girlfriend, etc.) in the adult client assessment. The history of working adults or college students with — 64 ADHD often reveal that adult clients?
- Change jobs or colleges frequently-This may be due to "boredom" or inability to complete routine tasks. Many employers also terminate employment when the individual fails to cope with task demands, to be punctual, or to sustain the ability to work towards goals. College students may drop out frequently and have difficulty with studying homework, and completing assignments on time.
- Procrastinate-Missed deadlines and difficulty completing tasks or ideas often dominate the work history of adult ADHD clients.
- Have interpersonal difficulties and poor social skills- Interpersonal difficulties are often noted by supervisors and coworkers and typically include "foot-in-mouth" statements reflecting impulsive verbal traits. — 66

Exhibit extreme fluctuations in behavior-These fluctuations characterize many with ADHD. Sometimes, they show inconsistent creativity or bursts of energy in completing certain tasks.

Family and Individual Psychiatric Histories — 58

Family and individual psychiatric histories help in making an accurate diagnosis. Specifically, family-genetic studies show a significant likelihood of several psychiatric conditions in first-degree relatives of children with ADHD. These include ADHD, affective and anxiety disorders, learning disabilities, conduct, oppositional, and antisocial disorders, as well as alcohol and substance abuse.

Family history may provide clues to diagnosis. For instance, someone whose parents have both been diagnosed with ADHD will be more likely to be diagnosed with ADHD. Children with parent having Bipolar Disorder are at higher risk for Bipolar Disorder. The related symptoms such as irritable mood, talkativeness, racing thoughts, distractibility, and impulsive behavior may be easily confused with ADHD.

Medical and Developmental History — 60

Clinicians should gather a thorough medical and developmental history to identify causal factors that may stem from certain medical conditions as well as to establish any pattern of ADHD maladaptive behavior. From a medical standpoint, there are several risk factors associated with ADHD that should be noted by the clinician. These include:
- Prenatal and postal difficulties such as toxemia, trauma, infection during pregnancy, or the baby having difficulty breathing, sucking or sleeping shortly after birth.
- Maternal substance abuse, during pregnancy.
- Poor maternal health.
- Vitamin and mineral deficiencies particularly alcohol and cigarettes symptoms, though foods do not accuse ADHD. Subclinical vitamin deficiencies can cause inattention and lowered performance on tests. Additionally, lead and cadmium metals can be absorbed into the brain and produce hyperactivity and learning disabilities.

Children with certain medical conditions, such as hyperthyroidism, seizures, Fetal Alcohol Syndrome, Pervasive Developmental Disorder, Neurofibromatosis, and allergies (e.g., corn, peanuts, milk), or genetic disorders, such as Turner Syndrome and Fragile X syndrome can have symptoms that mimic ADHD symptoms. Another common problem is the confusion between children's inattention to verbal stimuli and their hearing acuity.

Strategies for Assessing Changes Due to Treatment

An important principle of evaluating the effects of treatment is a multi-method approach, which uses three steps to evaluated the effects of treatment. These include: — 48

1. *Establishing target symptoms-*Many possible target symptoms can be assessed by gathering information from teachers, parents, and directly from the child. To evaluate the impact of therapy, assess the specific presentation of symptoms for a particular patient. Obtain specific examples of the symptoms through an interview.

2. *Domains of impairment-*Symptoms or behaviors are treated only if they create impairment in the client's life. The diagnostic interview elicits specific examples of how the target symptoms affect various domains of functioning. These specific examples provide the concrete situations against which subsequent therapeutic change will be judged.

Follow-up interviews form the basis of judgment about the impact of the treatment. Sometimes the symptom will change in one setting but not another. For example, fidgeting may be reduced while playing a game, but not while doing arithmetic homework.

3. *Measuring changes at different drug dosages-* To measure changes at different dosages, assess each symptom's impact on school, home, peers, and self, then compare current and initial states of functioning. Be cautious not to mistakenly compare the current state only with a precious client observation. When clinicians compare the current state with the initial state, they will better document small, incremental changes that occur as a result of the drug dosage over time.

Fig. 5.

| ADHD Symptoms of Inattention | If a symptom on the left is a problem, write in an example and check all boxes (for environment) in which the problem occurs. Check how often the problem occurs in the boxes on the right. | | How often does the problem occur? |
|---|---|---|---|
| a. often fails to give close attention to details or makes careless mistakes in schoolwork, work, or activities | ❏ home<br>❏ school<br>❏ social<br>❏ self | —70<br>72 | ❏ Infrequently<br>❏ 1-3 a week<br>❏ 1-3 a day<br>❏ almost all the time |
| b. often has difficulty sustaining attention in tasks or play activities | ❏ home<br>❏ school<br>❏ social<br>❏ self | | ❏ Infrequently<br>❏ 1-3 a week<br>❏ 1-3 a day<br>❏ almost all the time |
| c. often does not seem to listen when spoken to directly | ❏ home<br>❏ school<br>❏ social<br>❏ self | —74— | ❏ Infrequently<br>❏ 1-3 a week<br>❏ 1-3 a day<br>❏ almost all the time |
| d. often does not seem through and fails to finish schoolwork, chores, or duties | ❏ home<br>❏ school<br>❏ social<br>❏ self | | ❏ Infrequently<br>❏ 1-3 a week<br>❏ 1-3 a day<br>❏ almost all the time |
| e. often has difficulty organizing tasks and activities | ❏ home<br>❏ school<br>❏ social<br>❏ self | | ❏ Infrequently<br>❏ 1-3 a week<br>❏ 1-3 a day<br>❏ almost all the time |
| f. often avoids, dislikes or is reluctant to engage in tasks that require sustained mental effort | ❏ home<br>❏ school<br>❏ social<br>❏ self | | ❏ Infrequently<br>❏ 1-3 a week<br>❏ 1-3 a day<br>❏ almost all the time |
| g. often loses things necessary for tasks or activities | ❏ home<br>❏ school<br>❏ social<br>❏ self | | ❏ Infrequently<br>❏ 1-3 a week<br>❏ 1-3 a day<br>❏ almost all the time |
| h. is often easily distracted by extraneous stimuli | ❏ home<br>❏ school<br>❏ social<br>❏ self | | ❏ Infrequently<br>❏ 1-3 a week<br>❏ 1-3 a day<br>❏ almost all the time |
| i. is often forgetful in daily activities | ❏ home<br>❏ school<br>❏ social<br>❏ self | | ❏ Infrequently<br>❏ 1-3 a week<br>❏ 1-3 a day<br>❏ almost all the time |

26 © 2001 Compact Clinicals

62 ADHD Symptom Tracking System - page 1 64 66

Patient Name ______ Parent ______ Date ______

Patient Information:
Age:
Grade:
Teacher:
Ht:    68
Wt:
BP:

Assessment Interview

Fig. 6.

| ADHD Symptoms of Inattention | If a symptom on the left is a problem, write in an example and check all boxes (for environment) in which the problem occurs. Check how often the problem occurs in the boxes on the right. | | How often does the problem occur? |
|---|---|---|---|
| a. often fidgets with hands or feet or squirms in seat | ☐ home<br>☐ school<br>☐ social —32<br>☐ self | 34 | ☐ Infrequently<br>☐ 1-3 a week<br>☐ 1-3 a day<br>☐ almost all the time |
| b. often leaves seat in classroom or in other situations in which remaining seated is expected | ☐ home<br>☐ school<br>☐ social<br>☐ self | | ☐ Infrequently<br>☐ 1-3 a week<br>☐ 1-3 a day<br>☐ almost all the time |
| c. often runs about or climbs excessively in situations in which it is inappropriate | ☐ home<br>☐ school<br>☐ social<br>☐ self | —36— | ☐ Infrequently<br>☐ 1-3 a week<br>☐ 1-3 a day<br>☐ almost all the time |
| d. often has difficulty playing or engaging in leisure activities quietly | ☐ home<br>☐ school<br>☐ social<br>☐ self | | ☐ Infrequently<br>☐ 1-3 a week<br>☐ 1-3 a day<br>☐ almost all the time |
| e. often "on the go" or acts as if "driven by a motor | ☐ home<br>☐ school<br>☐ social<br>☐ self | | ☐ Infrequently<br>☐ 1-3 a week<br>☐ 1-3 a day<br>☐ almost all the time |
| f. often talks excessively | ☐ home<br>☐ school<br>☐ social<br>☐ self | | ☐ Infrequently<br>☐ 1-3 a week<br>☐ 1-3 a day<br>☐ almost all the time |
| g. often blurts out answers before questions have been completed | ☐ home<br>☐ school<br>☐ social<br>☐ self | | ☐ Infrequently<br>☐ 1-3 a week<br>☐ 1-3 a day<br>☐ almost all the time |
| h. often has difficulty awaiting turn | ☐ home<br>☐ school<br>☐ social<br>☐ self | | ☐ Infrequently<br>☐ 1-3 a week<br>☐ 1-3 a day<br>☐ almost all the time |
| i. often interrupts or intrudes on others | ☐ home<br>☐ school<br>☐ social<br>☐ self | | ☐ Infrequently<br>☐ 1-3 a week<br>☐ 1-3 a day<br>☐ almost all the time |

ADHD Symptom Tracking System - page 2

© 2001 Compact Clinicals

Assessment Interview

*Fig. 7.*

Patient Guidelines

How do I use my Copy of the ADHD Symptom Tracking System?

Receiving the best treatment for ADHD is a team effort between you and your physician. You can use this form to learn more about ADHD, communicate with your physician, and track improvement. Specifically:

1. Learn More About ADHD- Read the specific ADHD symptoms in column 1 of pages 1 & 2. These will help you understand specific symptoms and the brad scope of ADHD.

2. Communicate With Your Physician- Discuss with your physician ADHD symptoms you or your family member experience. Describe how any of the ADHD symptoms affect your home, work, school, social or personal life. With this information, your physician can target treatment to your specific needs.

3. Track Symptom Improvement-Tell your physician when and how symptoms improve - at different times of the day and/or in different settings such as home, work, during school, after school, during homework, or with family and friends. This information will help you and your physician determine the best treatment strategies for you and your family.

Where can I get More Information on ADHD?

The following organizations offer resources on ADHD:

The national organization, C.H.A.D.D., Children and Adults with ADD/ADHD may have a local support group in your city. 1-301-306-7070; www.chadd.org National Attention Deficit Disorder Association, www.add.org ADD Warehouse for publications on ADD/ADHD www.addwarehouse.com An internet resource site for women and girls with ADD, www.ADDvance.com

What are the Treatment Options for ADHD?

There are two basic approaches for treatment and management that target the symptoms of ADHD. One is behavior management. The other is medication. The combination of these tow main types of treatment is what is referred to as a *total treatment program.*

A total treatment program requires a coordinated effort among many people, including the child, the family, school personnel, physicians, and other health-care professionals. A total treatment program includes parent education and training in ADHD, behavior management techniques, an appropriate school environment, family counseling, and medication. The positive results that can be achieved make the extra effort all the more worthwhile.

Behavior management techniques are useful for parents and teachers, in home and school settings. Developing consistency across school, home, and community settings and among parents, teachers, and therapists is crucial to the success of behavioral treatment but can be a significant challenge to achieve.

Behavior management, as part of a total treatment program, is an important type of therapy for ADHD. Some behavioral adjustments suggested by the American Medical Association (AMA) included:

- Asking your child's teacher to move your child to the front of the room
- Establishing daily checklists
- Focusing on success
- Reinforcing your child's self-esteem Stimulants are the most frequently used medications for managing ADHD symptoms. These medications are effective in decreasing impulsivity and hyperactivity, and increasing attention. Approximately 70% to 80% of children and adults with ADHD respond positively to medications.

---

Trademark is contraindicated in patients with marked anxiety, tension, and agitation, since the medication may aggravate these symptoms; in patients known to be hypersensitive to methylphenidate or other components of the product; in patients with glaucoma; in patients with motor tics or family history or diagnosis of Tourette's syndrome; and during or following treatment with monoamine oxidase inhibitors.
Trademark should be given cautiously to patients with a history of drug dependence or alcoholism. Chronic abusive use can lead to marked tolerance and psychological dependence. (See Boxed Warning.)
Trademark should not be used in children under 6 years, since safety and efficacy in this age group has not been established.

| TM | Trademark Logo | ⟨ TM ⟩ Trademark Logo | 'Trademark Name' is a trademark of XYZ Corporation |

Fig. 8.

© 2001 Compact Clinicals — 92

ADHD Symptom Tracking System - page 2 — 82

Patient Name _______________

Refer to ADHD Assessment Interview form for problematic symptoms and rate progress as: N (no change); I (improved/still needs attention)/ or R (resolved) and add any helpful reference.

| ADHD Symptoms of Inattention | 1st Follow-up Date: ______ | 2nd Follow-up Date: ______ | 3rd Follow-up Date: ______ |
|---|---|---|---|
| a. poor attention to details | ☐N ☐I ☐R — 84 | ☐N ☐I ☐R | ☐N ☐I ☐R |
| b. poor attention span | ☐N ☐I ☐R — 86 | ☐N ☐I ☐R | ☐N ☐I ☐R |
| c. does not seem to listen | ☐N ☐I ☐R — 88 | ☐N ☐I ☐R — 90 — | ☐N ☐I ☐R |
| d. does not follow through | ☐N ☐I ☐R | ☐N ☐I ☐R | ☐N ☐I ☐R |
| e. difficulty organizing tasks | ☐N ☐I ☐R | ☐N ☐I ☐R | ☐N ☐I ☐R |
| f. poor sustained mental effort | ☐N ☐I ☐R | ☐N ☐I ☐R | ☐N ☐I ☐R |
| g. loses things | ☐N ☐I ☐R | ☐N ☐I ☐R | ☐N ☐I ☐R |
| h. easily distracted | ☐N ☐I ☐R | ☐N ☐I ☐R | ☐N ☐I ☐R |
| i. forgetful | ☐N ☐I ☐R | ☐N ☐I ☐R | ☐N ☐I ☐R |

| Symptoms of Hyperactivity/ Impulsivity | N = No change; I = Improved/still needs attention, R = resolved | | |
|---|---|---|---|
| a. fidgets | ☐ ☐ ☐ | ☐N ☐I ☐R | ☐N ☐I ☐R |
| b. leaves seat when shouldn't | ☐ ☐ ☐ | ☐N ☐I ☐R | ☐N ☐I ☐R |
| c. runs about excessively | ☐ ☐ ☐ | ☐N ☐I ☐R | ☐N ☐I ☐R |
| d. difficulty playing quietly | ☐ ☐ ☐ | ☐N ☐I ☐R | ☐N ☐I ☐R |
| e. "driven by a motor" | ☐ ☐ ☐ | ☐N ☐I ☐R | ☐N ☐I ☐R |
| f. talks excessively | ☐ ☐ ☐ | ☐N ☐I ☐R | ☐N ☐I ☐R |
| g. blurts out | ☐ ☐ ☐ | ☐N ☐I ☐R | ☐N ☐I ☐R |
| h. difficulty awaiting turn | ☐ ☐ ☐ | ☐N ☐I ☐R | ☐N ☐I ☐R |
| i. interrupts others | ☐ ☐ ☐ | ☐N ☐I ☐R | ☐N ☐I ☐R |

ADHD Follow-up Report    Continue on Back of Form ➡

*Fig. 9.*

© 2001 Compact Clinicals

ADHD Symptom Tracking System – page 2

| 1st Follow-up | 2nd Follow-up | 3rd Follow-up |
|---|---|---|
| Date: ___________ —94 | Date: ___________ —96 | Date: ___________ —98 |
| Parent: ___________ | Parent: ___________ | Parent: ___________ |
| Parent's age: ___________ | Parent's age: ___________ | Parent's age: ___________ |
| Grade: ___________ | Grade: ___________ | Grade: ___________ |
| Teacher: ___________ | Teacher: ___________ —100 | Teacher: ___________ |

Specific problem/concerns:        Specific problem/concerns:        Specific problem/concerns:

—102—

/104                  /106                  /108

Ht.   (   %) +or-      Ht.   (   %) +or-      Ht.   (   %) +or-
Wt.   (   %) +or-      Wt.   (   %) +or-      Wt.   (   %) +or-
BP:                   BP:                   BP:

—110—

Medications: —112         Medications:              Medications:
  Weekends: Yes__ No__      Weekends: Yes__ No__      Weekends: Yes__ No__
  summer:   Yes__ No__      summer:   Yes__ No__      summer:   Yes__ No__

Side Effects:              Side Effects:              Side Effects:
❏ Appetite                 ❏ Appetite                 ❏ Appetite
❏ Sleep          114       ❏ Sleep                    ❏ Sleep
❏ Mood changes             ❏ Mood changes             ❏ Mood changes
❏ Headaches                ❏ Headaches                ❏ Headaches
❏ Stomachaches             ❏ Stomachaches             ❏ Stomachaches
❏ Tics                     ❏ Tics                     ❏ Tics
❏ Other                    ❏ Other                    ❏ Other Notes/Treatment Changes     Notes/Treatment Changes     Notes/Treatment Changes
            \116                        \116                        \116

FIG. 11.

PATIENT CONDITIONAL DIAGNOSIS, ASSESSMENT AND SYMPTOM TRACKING SYSTEM

CROSS-REFERENCE TO RELATED APPLICATION

This application is a continuation of U.S. patent application Ser. No. 10/093,198, filed Mar. 7, 2002, now U.S. Pat. No. 7,008,378, entitled PATIENT CONDITIONAL DIAGNOSIS, ASSESSMENT AND SYMPTOM TRACKING SYSTEM.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The present invention is broadly concerned with a system and method for conditional diagnosis, assessment and symptom tracking of patients having behavioral health and/or physical disorders. More particularly, it is concerned with a system and method for providing a health care practitioner with diagnostic criteria and assessment techniques for a particular disorder, recording a treatment plan, and tracking patient symptoms and responses to the treatment plan in order to assess, optimize and document symptom improvement under the treatment plan, as well as providing the patient and clinician with an education and interaction tool for facilitating communication between patient and practitioner regarding the nature of the disorder and purpose and progress of the treatment.

2. Description of the Related Art

Health care practitioners or clinicians voluntarily document observation and treatment of their patients so that they can monitor their treatment plans and make appropriate revisions to optimize patient symptom improvement. Such documentation is also required so that the quality of their care can be monitored by federal and state agencies, such as Medicare and Medicaid, and various private accreditation agencies, such as the Joint Committee on the Accreditation of Health Care Organizations. Clinicians also need to maintain adequate documentation in order to respond to requests from third party insurers for substantiation of patient claims for reimbursement.

Health care practitioners are trained to identify the symptoms of a patient, make a diagnosis of a disorder or disease, assess the severity of the disorder, develop a plan for treatment of the patient and track the progress of the treatment plan. To assist them in documenting these steps, clinicians generally dictate their notes of each patient visit. The notes are subsequently transcribed and maintained in a confidential record, or so-called "chart". While the primary purpose of the chart is to assist the clinician with diagnosis and assessment of the patient's progress under the treatment plan, it also serves an important documentation function. Although the patient generally does not have access to the chart, information may be culled from it and provided to third parties such as insurance companies and various regulatory and accreditation agencies. Each of such third parties has its own documentary requirements, and any failure of the clinician to fully meet such requirements may result in negative consequences for both the clinician and the patient. For example, third party payors such as insurance companies frequently deny claims for reimbursement based on inadequate documentation of symptoms to support the diagnosis or progress under the treatment plan. And reimbursement may be denied for treatment which is expensive or long term in cases where progress cannot be demonstrated by familiar, objective methods, such as by laboratory testing.

In addition, such chart-type documentation methods produce a series of "snap shot" records of the patient's symptoms at each office visit. Over the course of treatment, the chart may become voluminous and time consuming for clinician review.

When a patient suffers from an injury or illness, a record of the patient's symptoms, diagnosis (whether the disorder exists), assessment (the severity of the condition once it is diagnosed) and the progress of the chosen treatment plan are relatively easy to document. However, when a patient suffers from physical symptoms having no observable underlying cause, or suffers from a disorder having behavioral or psychological symptoms, documentation of diagnosis, assessment and progress under the treatment plan can be substantially more difficult. Practitioners themselves may have difficulty tracking the effectiveness of treatment of such a patient.

In order to assist clinicians, various professional associations have developed criteria for use in establishing a diagnosis, conducting an assessment and evaluating the effectiveness of a treatment plan implemented by the practitioner. For example, the American Psychiatric association has developed the DSM-IV Diagnostic Criteria for Attention Deficit Hyperactivity Disorder (ADHD). A variety of diagnostic and assessment instruments have been implemented which employ such criteria.

Some instruments have been developed to assist in establishing a diagnosis, for example the Conners ADHD/DSM IV Scales. Some instruments, such as the Beck Depression Inventory, combine both diagnosis and assessment functions. Both of these types of instruments are generally in the form of questionnaires, which may be completed by a patient or by a health care practitioner during an interview with the patient. Such so-called self-reporting instruments include a set of predetermined questions which are answered by the patient. The responses may be forwarded to a testing center for visual or computerized scoring and the results returned to the patient's health care practitioner for interpretation. The responses may also be scored in the clinician's office. Alternatively, the health care practitioner may conduct a structured interview of the patient. As with self-reporting instruments, the patient's responses are scored and subsequently interpreted by the practitioner.

Once a conditional diagnosis and assessment have been made, the health care practitioner generally develops a treatment program consisting of prescribed medication and/or behavior management. Whether or not the diagnosis and assessment are conducted simultaneously and whether they are conducted by patient self-report or by structured interview, they provide a fixed record of the health status of the patient at the time the diagnosis and assessment are made. Some health care practitioners provide their patients with copies of the diagnosis and assessment scores. However, without clinical knowledge and experience, such scores generally provide a patient with little insight.

It is well known that the more targeted a treatment program is to a patient's own symptoms, the better the result. The effects of the treatment program on the patient's symptoms and development of any side-effects will determine whether the program requires modification. Thus, treatment is optimized by frequent periodic patient assessment during the course of the prescribed therapy. However, available assessment instruments provide one time, "snap shot" views, which are time consuming and require expensive subsequent scoring and analysis. Because they can only assess the patient's health status at the time of administration, they must be periodically readministered, scored and analyzed throughout the duration of the treatment program. Even then, the resulting multiplicity of scored assessment instruments in the patient's chart does not provide the clinician with a convenient, continuous summary of the patient's progress.

Some instruments, such as the Distressed Mood/Behavior Intervention Form have been developed for use as preprinted charts for institutionalized patients. These instruments are used by caregivers to document when a common behavioral symptom such as wandering occurs, the intervention, such as redirection, employed by the caregiver, and the initials of the caregiver observing the behavior. While such instruments provide a chart of patient behavior, they must be completed by the caregiver and do not include diagnostic and assessment criteria for any particular illness, or permit tracking of the patient's progress in response to a treatment program.

The diagnostic and assessment criteria for some disorders, such as ADHD, are complex and the assessment depends heavily on the patient's recollection. Consequently, a health care practitioner may have difficulty obtaining a complete record of all reportable factors, including symptoms, settings and frequency at every office visit. The complexity of the disorder may also leave patients confused and with unanswered questions about their disorder and their impairment may prevent them from organizing their thoughts during the brief office visit. Patients may also need general advice regarding alternative treatment options and where they can obtain additional information; or they may need more specific advice regarding how to keep track of their symptoms and communicate them to their health care practitioner so that complete information is provided. While patient care pamphlets are available to provide general information regarding many common disorders, they are not tailored to individual patients and they include no patient-specific symptom information. Patients generally receive little written information regarding their particular disorder and treatment plan and are provided with no written record of the initial assessment.

Accordingly, there is a need for a combination diagnostic and assessment tool that can be used as the basis for a dialog between a patient and practitioner during the office visit and which is aimed at tracking the patient's symptoms and targeting the treatment for those symptoms as they change over time. Such a tool is needed in order to document treatment progress for the clinician and the patient, as well as for third parties such as insurers and regulatory agencies. There is also a need for such a tool which is very easy to use in order to ensure that it will be used at every office visit. Regular usage of such a tool is necessary in order to track the progress of the treatment program so that the treatment can be promptly adjusted as necessary to optimize the outcome.

SUMMARY OF THE INVENTION

The present invention relates generally to a method for conditionally diagnosing a mental or physical disorder in a patient and assessing and tracking the symptoms of the patient during treatment for the disorder. The method involves providing an interview instrument implemented as a computer program, generating a screen display, and accessible and used by either or both of the clinician and the patient to record and track the symptoms, the interview instrument having a list of symptoms and diagnostic and assessment information for a selected disorder. A clinician conducts a first interview of the patient to identify and assess the patient's symptoms of the disorder in accordance with the list of symptoms and diagnostic and assessment information. The clinician then records the patient's symptoms and the clinician's assessment of the symptoms on the interview instrument. Alternately, the patient records the patient's symptoms on the interview instrument and the clinician then conducts a first interview of the patient. The clinician develops a diagnosis and treatment plan for the disorder and records them on the interview instrument. The clinician conducts one or more subsequent interviews of the patient for identifying and assessing the patient's symptoms; and the clinician records changes in the patient's symptoms on the interview instrument for documenting the effects of the treatment plan.

The interview instrument includes joint use, diagnostic, patient-use and follow-up portions. The joint-use portion includes a list of symptoms and assessment criteria and space for recording the patient's symptoms as well an assessment of the symptoms. The diagnostic portion includes diagnostic information for a preselected disorder as well as space for recording a treatment plan. The patient-use portion includes instructions for communicating with the clinician and educational information about the disorder. The follow-up portion includes the listing of symptoms as well as spaces for recording changes in the patient's symptoms over time, under the treatment plan.

Objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a plan view of a first side of a first page of a chart copy of a patient assessment interview form for use in a patient conditional diagnosis and assessment tool in accordance with the present invention.

FIG. 2 is a plan view of a first side of a second page of a chart copy of the patient assessment interview form shown in FIG. 1.

FIG. 3 is a plan view of a second side of the first page of the chart copy of a patient assessment interview form shown in FIG. 1 including diagnostic criteria, Clarifying Information and Assessment Techniques.

FIG. 4 is a plan view of a second side of the second page of the chart copy of a patient assessment interview form shown in FIG. 2, including continued Assessment Techniques and Strategies for Assessing Changes Due to Treatment.

FIG. 7 is a plan view of a second side of the first page of a patient copy of the patient assessment interview form shown in FIG. 5, showing Patient Guidelines.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 8:
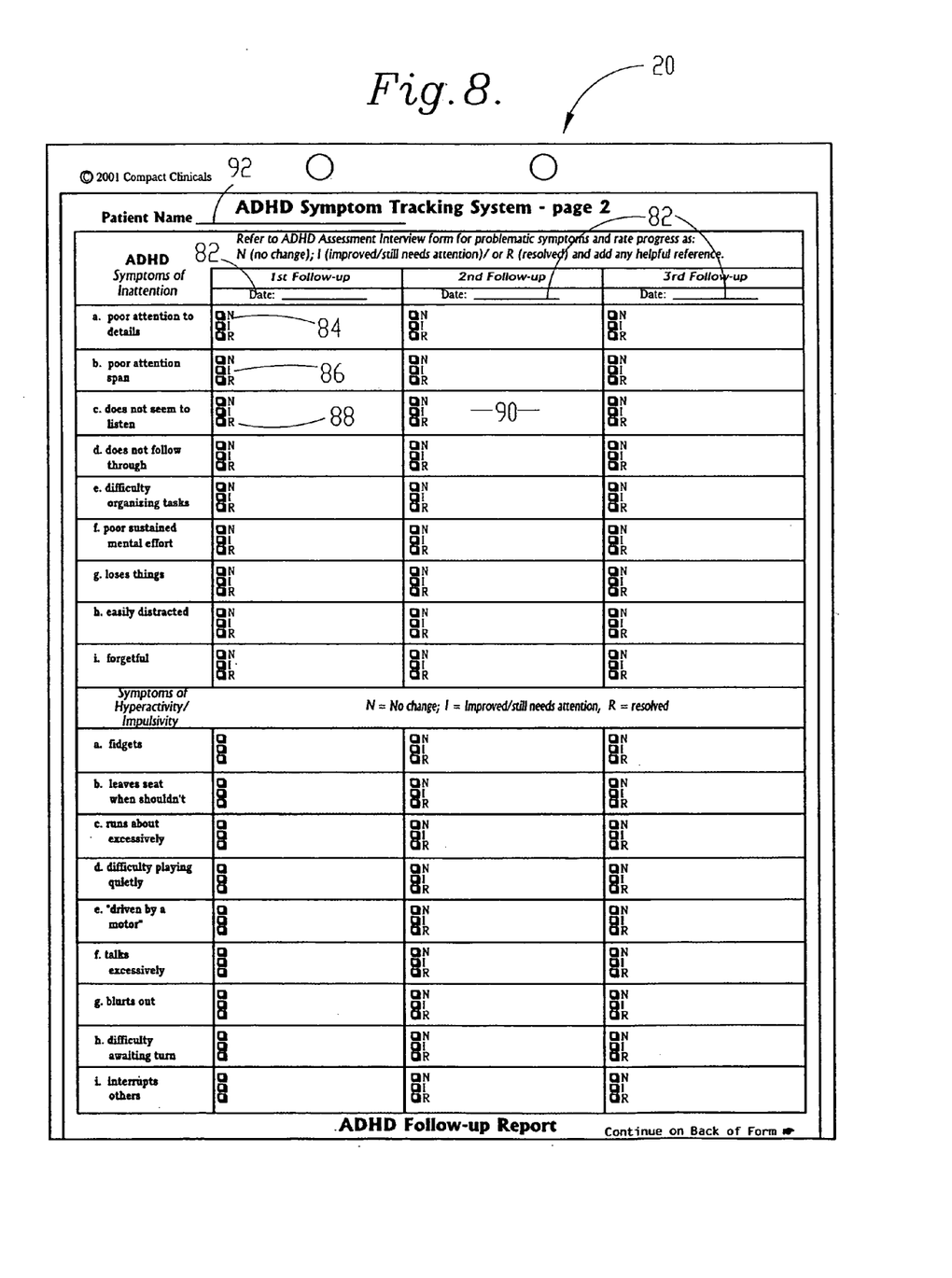
FIG. 8 is a plan view of a first side of an ADHD Follow-up Report.
Figure 9:
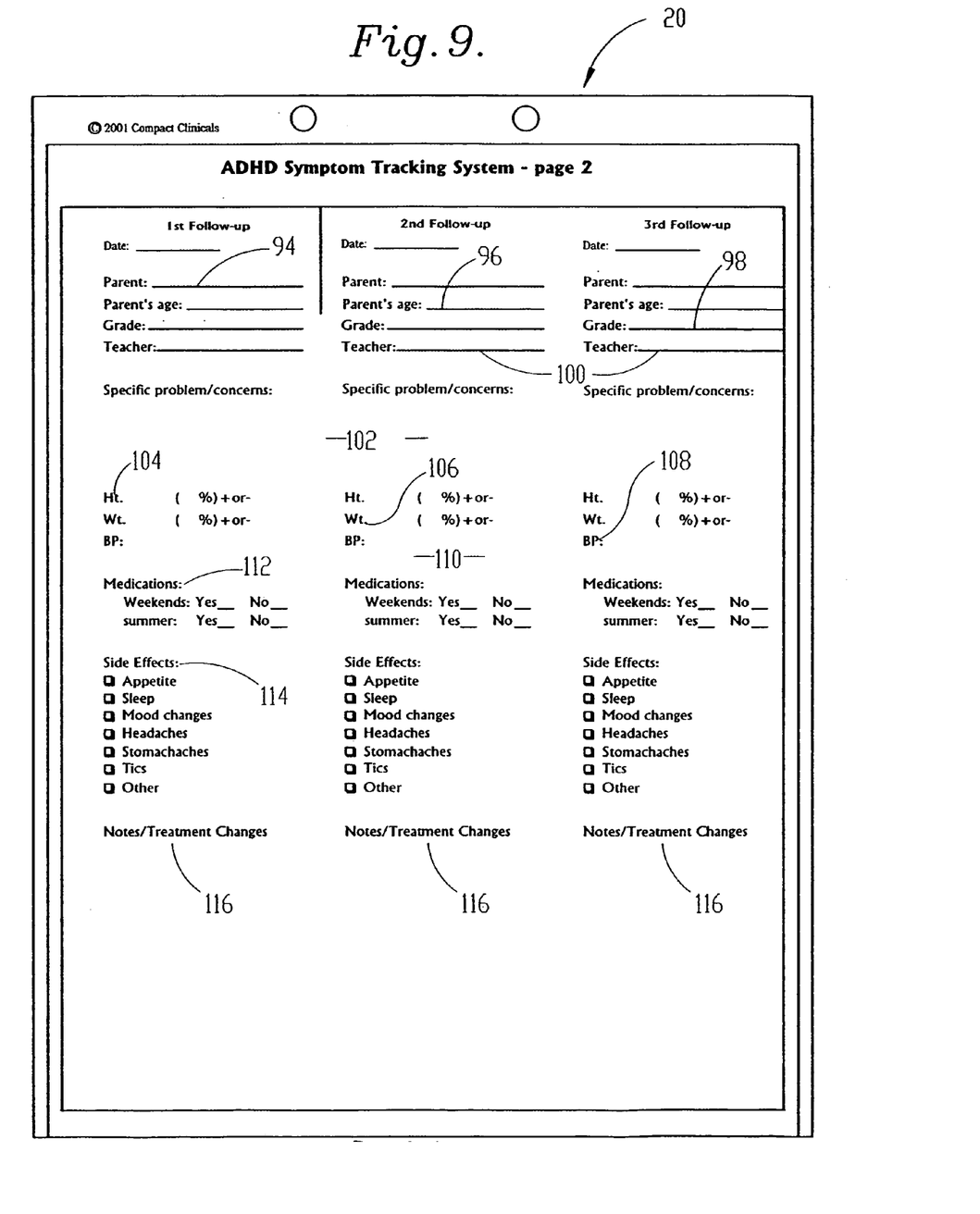
FIG. 9 is a plan view of a second side of the Report shown in FIG. 8.
Figure 10:
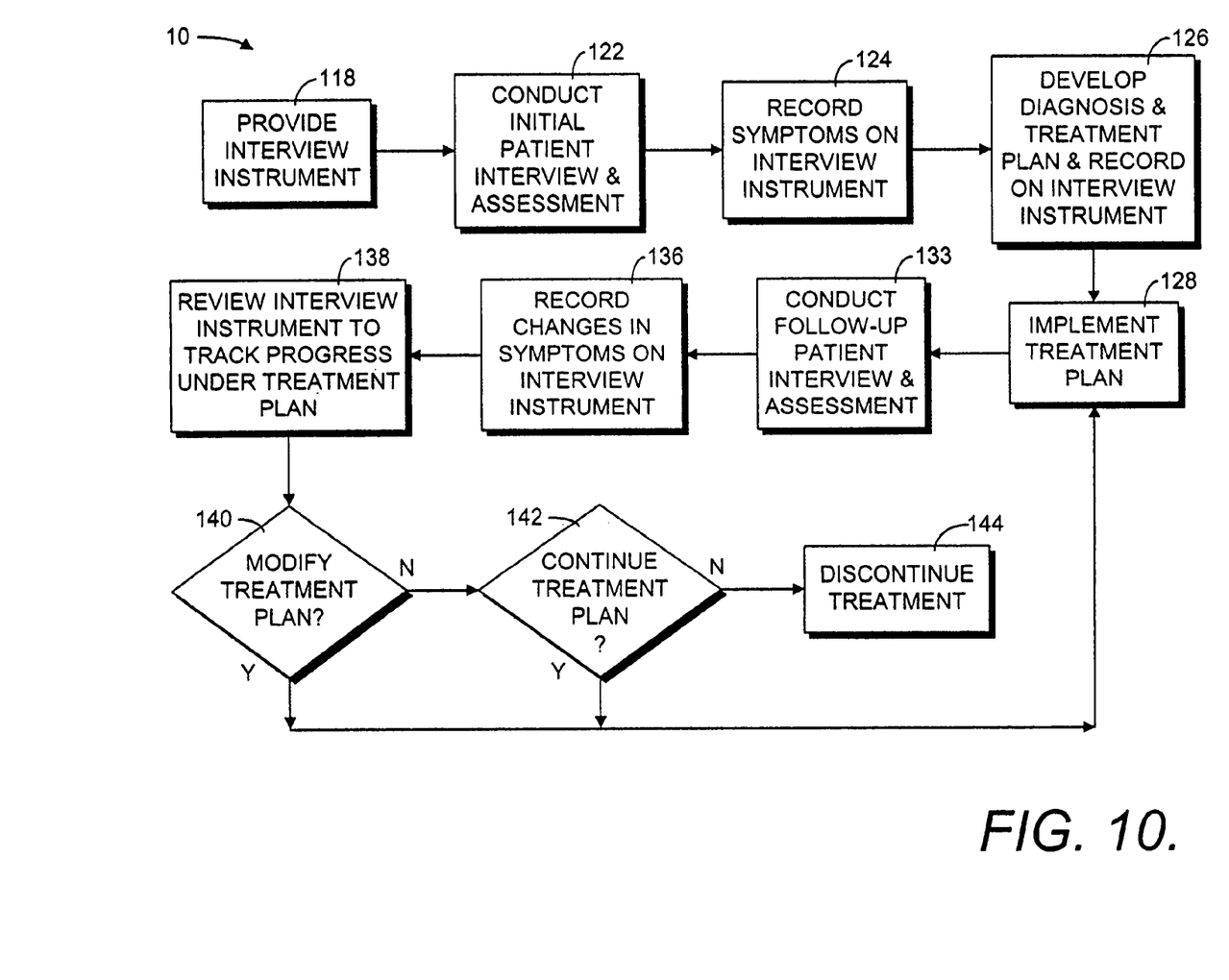
FIG. 10 is a simplified flow diagram showing steps of a patient conditional diagnosis, assessment and symptom tracking system in accordance with the invention.
Figure 11:
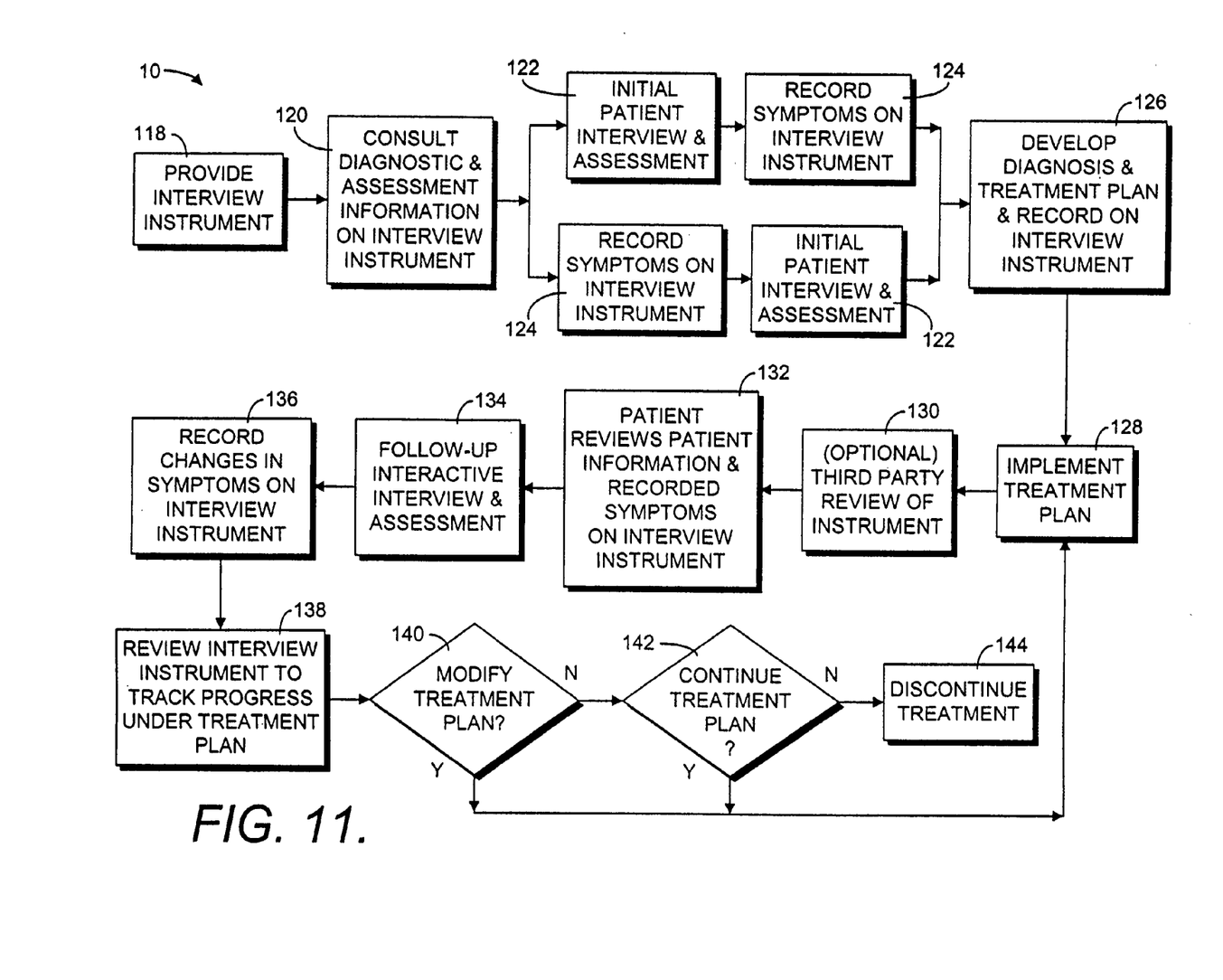
FIG. 11 is a more detailed flow diagram showing steps of the system depicted in FIG. 10.

Referring now to the drawings, FIGS. 10 and 11 depict a patient conditional diagnosis, assessment and symptom tracking method 10 in accordance with the present invention. FIGS. 1–9 depict an exemplary patient assessment interview instrument 12 for use in diagnosing patients with Attention Deficit Hyperactivity Disorder (ADHD). The interview instrument 12 includes a joint-use portion 14 (FIGS. 1–2 except spaces 50 and 52 and FIGS. 5–6), a diagnostic or clinician-use portion 16 (FIGS. 3–4 and boxes 50 and 52 of FIGS. 1–2), a patient-use portion 18 (FIG. 7), and a follow-up portion 20 (FIGS. 8–9).

Referring now to FIGS. 1–2 and 5–6, the joint-use portion 14 is designed for use by both the clinician and the patient. It includes identifying information in the form of a patient name space 22, a parent name space 24, date space 26 and a patient information space 28 for recording information relevant to diagnosis and treatment, such as age, grade, teacher, height, weight and blood pressure. It also includes a listing of the symptoms 30 with adjacent check boxes for recording the diagnostic environment or setting 32 and frequency assessment 34. Advantageously, the joint use portion 14 combines the information which is needed for diagnosis into a single record which may be easily reviewed by both the clinician and the patient. A space 36 is provided to enter examples of the symptoms, including the severity of the impairment. The joint use portion 14 may be completed by the clinician during a structured interview, or it may be completed by the patient. The joint use portion 14 also includes title and pagination indicia 38.

The diagnostic or clinician-use portion 16 shown in FIGS. 3–4 includes diagnostic and assessment information for a selected illness or disorder for use by a clinician. The information in this portion 16 is provided to educate and assist the clinician in reaching a conditional diagnosis and includes instructions 40 for using the interview instrument 12 to implement the tracking system and method 10. Diagnostic criteria 42 are provided for a preselected disorder or illness, including a listing of specific symptoms 30, diagnostic clarifying information 44 for use by the clinician in evaluating the symptoms 30, assessment techniques 46 for use by the clinician in assessing the symptoms 30, impairment and treatment response strategies 48 for assessing changes attributable to treatment. The clinician-use portion 16 also includes space for entry of Notes 50 and a Treatment Plan 52 by the clinician. These spaces are blocked out on the joint use-portion depicted in FIGS. 5 and 6, so that the Notes 50 and Treatment Plan 52 entered into these spaces by the clinician will not be automatically transferred to the pages distributed to the patient.

The diagnostic criteria 42, such as "Symptoms must have persisted for at least 6 months to a degree that is maladaptive and inconsistent with developmental level," and symptoms 30, such as "often has difficulty sustaining attention in tasks or play activities" may be derived from a diagnostic manual for psychiatric disorders, such as the *Diagnostic and Statistical Manual of Mental Disorders*(DSM) published by the American Psychiatric Association, or from any other recognized source. In the case of physical illnesses or disorders, the diagnostic criteria 42 may be derived from a medical diagnostic manual such as *The International Classification of Diseases* (ICD), published by the World Health Organization.

The diagnostic clarifying information 44, includes information specific to the preselected disorder necessary for evaluating the symptoms 30 once they are identified. In the exemplary interview instrument 12 for ADHD, diagnostic clarifying information 44 includes information regarding age of onset of the disorder, number and severity of the symptoms, pervasiveness and persistence of the impairment and persistence of the symptoms 30 designed to aid the clinician making a conditional differential diagnosis. Depending on the preselected disorder, the diagnostic clarifying information 44 may include any other factors recognized to be relevant to evaluation of the symptoms 30.

Although definitive diagnostic tests are available for some disorders, others like ADHD can only be diagnosed following careful assessment of the patient's history and symptoms 30. The interview instrument 12 includes assessment techniques 46 for assisting the clinician in assessing symptoms 30 of the preselected disorder, impairment of the patient attributable to the symptoms 30 and treatment response. Assessment techniques 46 may include interview and history techniques 54 designed to assist the clinician in gathering a complete history necessary to differentiate between situational problems, other disorders and a preselected disorder, such as ADHD. Assessment techniques 46 may also include observation techniques 56 for observing the patient's functioning in a plurality of environments, the family and psychiatric history 58 and medical history 60, which may indicate a likelihood of developing the disorder, identify causal factors, or provide other clues to diagnosis.

Strategies 48 for assessing changes attributable to implementation of a treatment plan include establishing target symptoms 62 and domains of impairment 64 and measuring changes at different drug dosages 66.

Although the term clinician is used herein for consistency, the method 10 and assessment instrument 12 may also be used to good effect by any behavioral or medical practitioner, such as physicians, psychologists, counselors, social workers, speech pathologists, physician's assistants, nurse practitioners, as well as teachers and therapists.

The patient use portion 18 of the instrument 12 is shown in FIG. 7 to include instructions 68 for use of the interview instrument 12. The instructions 68 include directives to learn 70 about the disorder, communicate 72 with the clinician and use the interview instrument 12 to track symptom improvement 74. Depending on the preselected disorder, additional directives may also be included. The patient use portion 18 also includes a patient information section 76 including contact information for organizations that offer resources directed to the disorder and a treatment section 78 that describes the accepted treatment approaches for the disorder. Pharmaceutical information 80 appropriate to the disorder may also be included. The pharmaceutical information 80 may include names of therapeutic agents approved for use in treatment of the disorder and information about dosage, administration, contraindications and warnings. The pharmaceutical information 80 may be accompanied by advertising indicia 81 of one or more selected pharmaceutical companies and the trade names of their therapeutic agents which may be suitable for use in treatment of the disorder. While the pharmaceutical information 80 is preferably printed on the patient-use portion 18 to inform patients of available pharmaceuticals for treating the disorder, this information may also be printed on the clinician-use portion 16.

The follow up report 20 is depicted in FIGS. 8 and 9 to include a plurality of lists of the symptoms 30 of the disorder with adjacent date spaces 82 for entry of the date of each follow-up visit. Adjacent the symptoms 30 are check boxes for No change 84, Improved/still needs attention 86 and Resolved 88. It is foreseen that, for some disorders, a check box indicating regression (not shown) may also be provided. A note space 90 is provided so that the clinician may indicate environmental, time, frequency or any other relevant differences in symptom improvement, e.g. that the symptom 30 is more improved at school than at home or that the symptom 30 is more improved in the morning than later in the day. The Follow-up report 20 includes lines for recording certain patient information such as name 92, parent 94, patient's age 96, grade 98, teacher 100 as well as a note space 102 for entry of any specific problems or concerns of the clinician. Space is also provided for recording physical characteristics such as a height space 104, weight space 106, blood pressure space 108 for recording blood pressure as well as any blood chemistry, such as, for example, serotonin levels, which may be relevant to tracking drug therapy. A medication information space 112 is provided for recording medication information relevant to the disorder, such as whether the medication is continued over weekends and during the summer. A listing of relevant medication side effects with adjacent check boxes 114 is also provided. The follow-up report 20 also includes space 116 for clinician notes/treatment changes, such as adjustment of medication dosage, recommendations for additional therapy such as behavioral therapy and any other treatment recommendations. The follow-up report 20 thus provides a concise record over time of the patient's progress under the treatment plan. The follow-up report 20 is designed primarily for review by the clinician in evaluating the patient's progress. However, it may also be distributed to the patient, so that the patient can review the progress and use this information to better communicate changes in their symptoms 30 to the clinician.

While the exemplary interview instrument 12 addresses two variants of a disorder which frequently occur in combination, Attention Deficit Disorder with or without Hyperactivity, it may also be designed to address other disorders, either singly or in groups of two or more. It may be employed for treatment of patients having some symptoms of any of a number of mental or physical disorders or illnesses, such as anxiety, dementia, disorders of the central nervous system, eating disorders, elimination disorders such as enuresis and encopresis, headaches and migraines, mood disorders such as Bipolar Disorder and Depression, psychoses such as Schizophrenia, sleep disorders, substance abuse, and chronic conditions such as Diabetes and Asthma. Those skilled in the art will appreciate that the system of the present invention can be employed for virtually any conditionally diagnosable mental or physical illness or disorder or combination thereof.

The interview instrument 12 may be implemented as either a printed booklet of tear-sheets or as a computer program generating a video display. FIGS. 1–9 depict the respective pages or screen displays. In booklet form, the exemplary ADHD interview instrument 12 includes two pairs of stacked pages and a third page for the follow-up portion 20. The pages are constructed so that FIGS. 1 and 3 depict respective first and second sides of a first page to be retained by a clinician and FIGS. 2 and 4 depict respective first and second sides of a second page to be retained by the clinician. In similar fashion, FIGS. 5 and 7 cover respective first and second sides of a first page to be retained by a patient and FIGS. 6 and 7 cover respective first and second sides of a second page to be retained by the patient. FIGS. 8 and 9 cover respective first and second sides of a follow-up report 20 to be retained by the clinician as documentation of the progress of the patient. In this manner, the educational material depicted in FIGS. 3 and 4 is imprinted on the reverse sides of the pages to be retained by the clinician and the educational material depicted in FIG. 7 is imprinted on the reverse side of the pages to be distributed to the patient. Where the patient educational material can be fitted onto a single page, as is shown in FIG. 7, then it may be imprinted on the reverse side of each page to be retained by the patient. It is also foreseen that the reverse side of one of the pages could be left blank, or lines for patient notes. Depending upon the length of the joint-use portion 14 and the length of the clinician-use and patient-use educational portions, it may not always be feasible to print the respective clinician and patient education portions on the reverse of the clinician-use 16 or patient-use 18 portions. In such instances, additional pages may be required or the information may be edited for length.

Figure 5:
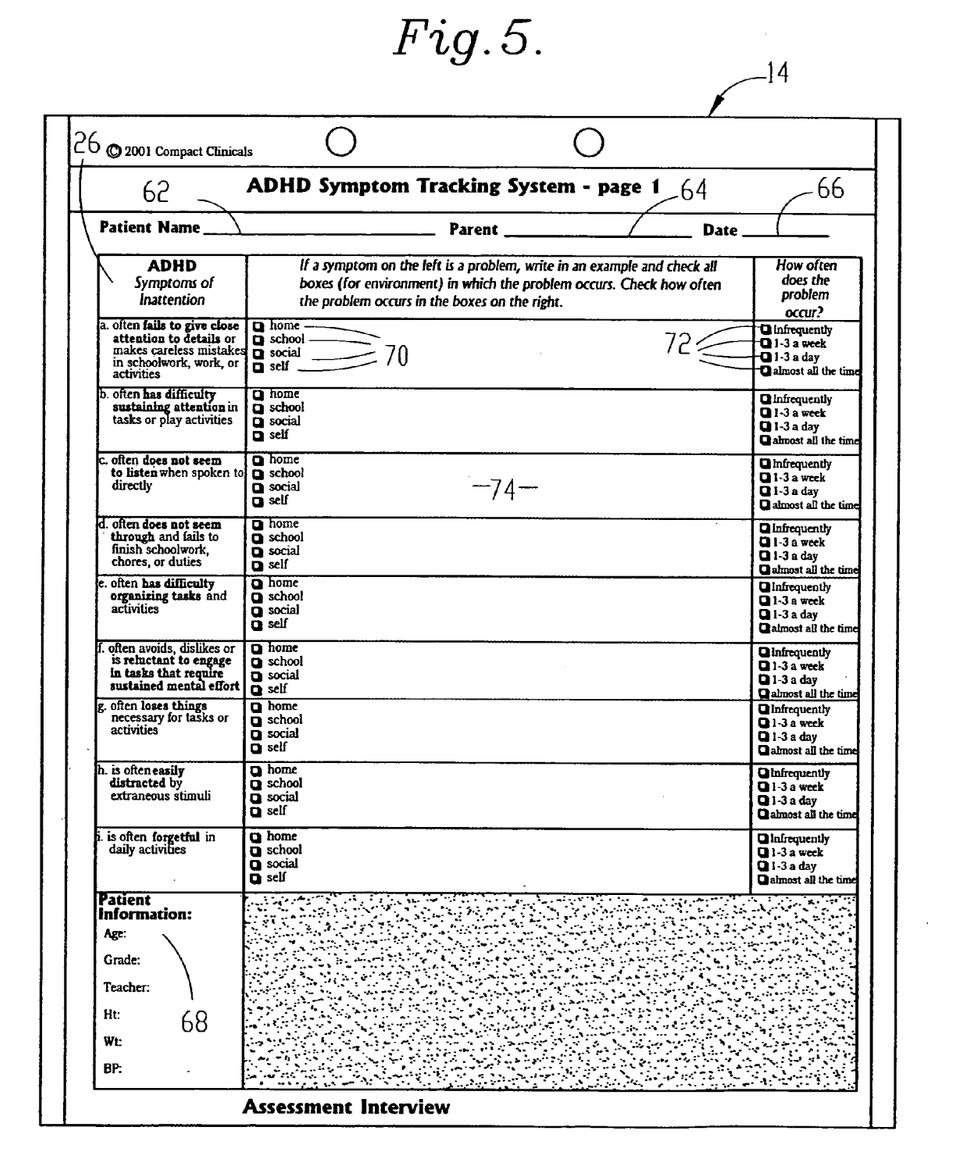
FIG. 5 is a plan view of a first side of a first page of a patient copy of the patient assessment interview form similar to the form shown in FIG. 1.
Figure 6:
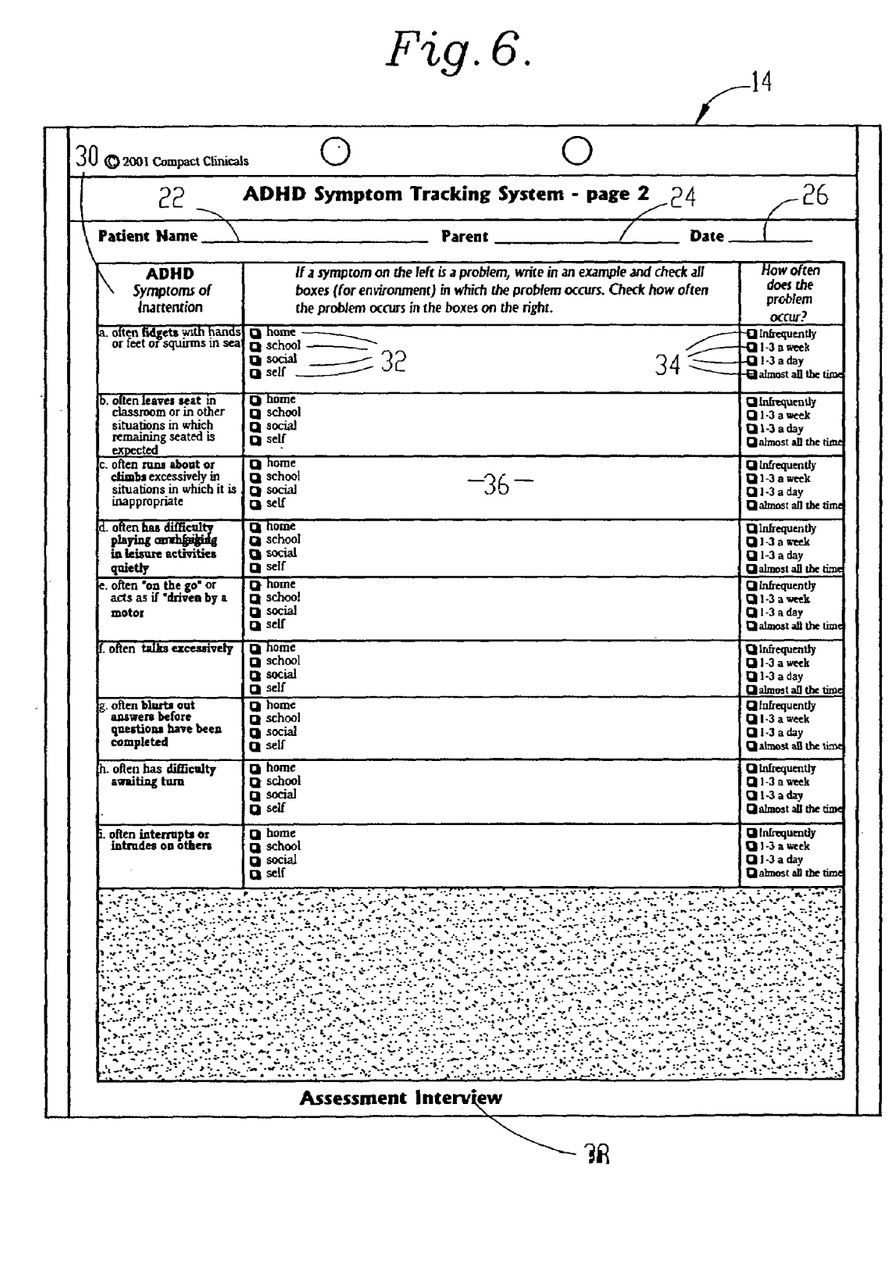
FIG. 6 is a plan view of a first side of a second page of a patient copy of the patient assessment interview form shown in FIG. 5.

A first Page 1 depicted in FIG. 1 is stacked atop a second Page 1 depicted in FIG. 5. A first page 2 is depicted in FIG. 2 and is stacked atop a second page 2 depicted in FIG. 6. The pages are constructed of so-called "carbonless" paper, so that entries on the first page 1 depicted in FIG. 1 in the setting and frequency check boxes 32 and 34 and notations in the space 36 for description of symptoms and examples are automatically transferred into the corresponding spaces on the second page 1 depicted in FIG. 5. Similarly, entries on the first page 2 depicted in FIG. 2 will be automatically transferred into the corresponding spaces on the second page 2 depicted in FIG. 6.

All of the pages of the interview instrument 12 are of approximately the same size, which may be any suitable size, such as, for example about 8½ inches by about 11 inches, except that the pairs of first and second pages and the follow-up report 20 may be progressively offset from each other by a short distance and imprinted with a title and/or pagination indicia, in the manner of an index. This arrangement serves to facilitate tear-sheet type removal of the copies of pages 1 and 2 by the clinician for distribution to the patient.

The symptoms 30 are arranged on the page fronts with adjacent boxes for indicating the environments described in the diagnostic criteria 42 and assessment techniques 46. The diagnostic criteria 42 and symptoms 30 are elucidated on the reverse side of the pages.

The previously described interview instrument 12, as shown in FIGS. 1–9 is adapted for use in a diagnosis, assessment and symptom tracking system or method 10.

FIG. 10 is a flow diagram with blocks representing the following steps of a simplified embodiment of the method 10: providing the clinician with an interview instrument, block 118; conducting an initial patient interview and assessment, block 122; recording symptoms on the interview instrument, block 124; developing a diagnosis and treatment plan and recording the plan on the interview instrument, block 126; implementing the treatment plan, block 128; conducting a follow-up patient interview and assessment, block 133; recording changes in symptoms on the interview instrument, block 136; reviewing the interview instrument to track progress of the patient under the treatment plan, block 138; modifying the treatment plan, block 140; and, alternatively, continuing the treatment plan, block 142 or discontinuing the treatment, block 144. As previously discussed, recording symptoms on the interview instrument, block 124 may be undertaken by the patient, and in such cases precedes conducting an initial patient interview and assessment, block 122.

In more detail, as shown in FIGS. 10 and 11, block 118 corresponds to providing the clinician with an interview instrument specially designed for diagnosis of a selected disorder and previously described in detail in association with reference numeral 12. The interview instrument 12 includes a joint use portion 14 for use by both the clinician and the patient, a diagnostic portion 16 for use by the clinician, a patient-use portion 18 for use by the patient, and a follow-up portion 20 for use by the clinician. While it is useful to organize the interview instrument 12 in this manner, such usage designations are not hard and fast. Any portion of the instrument may be considered to be a joint-use portion 14 where joint use may enhance the interactive nature of the interview and assessment or is likely to improve the treatment outcome.

The diagnostic portion 16 of the instrument 12 includes instructions 40, a list of symptoms 30 and diagnostic and assessment educational information about the disorder for clinician reference. The diagnostic and assessment information includes diagnostic criteria 42, diagnostic clarifying information 44 and assessment techniques 46.

The clinician consults the diagnostic and assessment information contained on the interview instrument, block 120 and conducts the initial interview and assessment, block 122 in accordance with the list of symptoms 30 and the diagnostic and assessment information contained in the interview instrument 12. The clinician next records the symptoms 30, the environment 32 in which they occur and the clinician's assessment of the patient's symptoms on the joint-use portion of the interview instrument, block 124. In some instances, it may be desirable to employ the space 36 for recording the exact words used by the patient to describe the symptoms. It is also foreseen that the patient may participate in this step by recording the symptoms, block 124. It is also foreseen that the instrument 12 may be implemented as a computer program, generating a screen display, which may be accessed and used by either or both of the clinician and the patient to record the symptoms 30. In such instances, the clinician may consult the record of the symptoms 30 prior to conducting the initial patient interview and assessment, block 122.

The clinician next identifies target symptoms for treatment and develops a treatment plan for treatment of the disorder and records the treatment plan on the interview instrument, block 126. The clinician may refer to the recorded symptoms 30, environment 32, frequency 34 and any severity information recorded on the interview instrument 12 in order to identify the target symptoms. The treatment plan may include medical procedures such as surgery, physical or behavioral therapy, administration of therapeutic agents as well as periodic testing, such as blood chemistry, ECG, blood pressure, or any other suitable treatment. The treatment plan is implemented, block 128 and in some instances the interview instrument may be reviewed by a third party, block 130. Third party review may be conducted by private or public insurers, such as Medicare and Medicaid, in order to determine whether and to what extent charges incurred by the patient for the interview and subsequent treatment will be reimbursable, or it may be conducted by state or federal regulatory agencies charged with reviewing quality of patient care.

The clinician distributes both the joint-use 14 and patient-use 18 portions of the instrument 12 to the patient. The patient use portion 18 includes instructions 68, patient educational information about the disorder 76 and a summary of treatment options 78. The patient next reviews at step 132 the patient information and the recorded symptoms 30 on the interview instrument 12. Such patient review enhances communication between the clinician and the patient.

At step 134 the clinician reviews the interview instrument 12 and conducts an interactive follow-up interview of the patient including assessment of the symptoms. Educated by review of the patient information and recorded symptoms on the interview instrument in block 132, the patient is better equipped to identify symptoms of the disorder as they are experienced as well as their environment and frequency. This improves the accuracy of the information garnered during the interview process and the communication of the information to the clinician for recording on the interview instrument 12. It also improves the quality of the patient's choices regarding treatment options and the patient's participation in the treatment itself.

The clinician next records at step 136 any changes in the patient's symptoms on the follow-up report portion 20 of the interview instrument 12. The clinician reviews the interview instrument to 12 track the progress of the patient under the treatment plan at step 138. This review may cause the clinician to determine that the treatment plan is appropriate and should be continued, blocks 140, 142 and 128, that the treatment plan has been accomplished and can be discontinued, blocks 140, 142 and 144, or that the treatment plan should be modified, blocks 140, 128.

In this manner, the interview instrument 12 functions as a dialog tool between the patient and clinician for improving diagnosis and assessment of a disorder or illness across multiple patient care visits. The follow-up report portion 20 of the interview instrument 12 provides documentation of the patient's progress across multiple visits. The follow-up report serves as a tracking tool for third parties who may have an interest in determining whether the patient is making progress under the treatment plan as well as documentation.

It is to be understood that while certain forms of the present invention have been illustrated and described herein, it is not to be limited to the specific forms or arrangement of parts described and shown.

What is claimed and desired to be secured by Letters Patent is as follows:

1. A method for conditionally diagnosing a selected disorder in a patient and assessing and tracking symptoms of the patient during treatment for the disorder, comprising the steps of:
   a. providing an interview instrument implemented as a computer program generating a screen display and accessible and usable by both of a clinician and a patient to record and track symptoms, said interview instrument including diagnostic and assessment information for a selected disorder, a joint-use portion for use by both said clinician and said patient and a follow-up portion, said diagnostic and assessment information, said joint-use portion and said follow-up portion each including a list of symptoms of said selected disorder;

b. a clinician conducting a first interview of said patient for identifying and assessing the patient's symptoms of said disorder in accordance with said list of symptoms of said selected disorder and said diagnostic and assessment information;

c. said clinician selecting said patient's identified symptoms from said list of symptoms on said joint-use portion and recording said symptoms and an assessment of said patient's identified symptoms by said clinician on said joint-use portion; and said patient reviewing said joint-use portion and recording revised identified symptoms or assessments on said joint-use portion and/or selecting and recording additional symptoms on said joint-use portion;

d. said clinician developing a diagnosis of said disorder based on said recorded symptoms, developing a treatment plan for treatment of said disorder, and recording said treatment plan on said interview instrument;

e. said clinician conducting a subsequent interview of said patient for assessing changes in symptoms of said patient by reference to said list of symptoms on said follow-up portion; and f. said clinician recording said changes in symptoms of said patient on said follow-up portion of said interview instrument for tracking effects of said treatment plan.

2. The method in claim 1, wherein said interview instrument further includes a patient information portion.

3. The method of claim 1 further including the step of:
a. said clinician identifying target symptoms of said patient for treatment.

4. The method in claim 1 including the steps of:
a. said clinician distributing a copy of the recorded patient's symptoms, an assessment of said recorded patient's symptoms by said clinician and a patient information portion to said patient; and
b. said patient reviewing said copy and said patient information portion for learning about said disorder and better communicating with said clinician.

5. The method as set forth in claim 1 wherein said patient records symptoms of said selected disorder on said joint-use portion before said clinician conducts said first interview.

6. The method as set forth in claim 1 wherein the step of recording said patient's identified symptoms and said clinician's assessment of said patient's identified symptoms on said joint-use portion further includes the step of:
a. said clinician recording the words used by said patient to describe said identified symptoms.

7. A method for conditionally diagnosing a selected disorder in a patient and assessing and tracking symptoms of the patient, comprising the steps of:
a. providing an interview instrument implemented as a computer program generating a screen display and accessible and usable by both of a clinician and a patient to record and track symptoms; said interview instrument including a diagnostic portion for use by a clinician, a patient-use portion for use by said patient, a joint-use portion for use by both said clinician and said patient, and a follow-up portion for use by said clinician; said diagnostic portion of said interview instrument including symptom, diagnostic and assessment information for a selected disorder, said joint-use portion and said follow-up portion each including a list of symptoms of said selected disorder; said patient-use portion of said interview instrument including educational information about said disorder;

b. said clinician reviewing said diagnostic and assessment information, interviewing said patient, identifying and recording patient symptoms of said disorder on said joint-use portion of said interview instrument by reference to said list of symptoms and an environment in which each of the identified symptoms occurs to create a record of said patient symptoms; said patient reviewing said joint-use portion and recording revised identified symptoms or environments on said joint-use portion and/or recording additional symptoms on said joint-use portion; and said clinician identifying target symptoms for treatment;

c. said patient reviewing said educational information on said patient-use portion of said interview instrument and reviewing said recorded symptoms; and d. said clinician again interviewing said patient, said patient reporting changes in symptoms of said patient, and said clinician recording said changes in symptoms of said patient on said follow-up portion of said interview instrument by reference to said list of symptoms on said follow-up portion for documenting effects of said treatment.

8. The method as set forth in claim 7 wherein the step of interviewing said patient and recording effects of said treatment on said identified symptoms on said follow-up portion of said interview instrument is repeated.

9. The method as set forth in claim 7 further including the step of:
a. said clinician prescribing a medication as part of said treatment and recording medication side effects on said patient.

10. The method as set forth in claim 7 further including the step of:
a. said clinician recording additional patient information.

11. The method as set forth in claim 7 further including the step of:
a. submitting said joint-use and said diagnostic portions of said interview instrument to a health care insurer as documentation for reimbursement for providing care to said patient.

12. The method as set forth in claim 7, further including the step of:
a. submitting said follow-up portion of said interview instrument to a health care insurer as documentation for reimbursement for providing continuing care to said patient.

13. The method as set forth in claim 7 wherein said patient records symptoms of said selected disorder on said joint-use portion before said clinician conducts a first interview.

* * * * *